United States Patent [19]

Resnick et al.

[11] 4,453,263
[45] Jun. 5, 1984

[54] CONSTANT POTENTIAL H-V GENERATOR

[75] Inventors: Theodore A. Resnick; Walter A. Dupuis, both of Cleveland Heights; Anthony Palermo, Jr., South Euclid, all of Ohio

[73] Assignee: Picker Corporation, Cleveland, Ohio

[21] Appl. No.: 335,591

[22] Filed: Dec. 30, 1981

Related U.S. Application Data

[63] Continuation of Ser. No. 81,779, Oct. 4, 1979, abandoned.

[51] Int. Cl.³ .............................................. H05G 1/32
[52] U.S. Cl. ..................................... 378/112; 323/227
[58] Field of Search ................. 378/112, 92; 323/227, 323/291

[56] References Cited

U.S. PATENT DOCUMENTS

| | | | |
|---|---|---|---|
| 3,325,645 | 6/1967 | Splain | 378/112 |
| 3,333,104 | 7/1967 | Bougle | 378/92 |
| 3,361,954 | 1/1968 | Jorgensen | 323/227 |

FOREIGN PATENT DOCUMENTS

| | | | |
|---|---|---|---|
| 2802451 | 7/1979 | Fed. Rep. of Germany | 378/112 |
| 2226971 | 11/1974 | France | |
| 2415415 | 8/1979 | France | |
| 2415416 | 8/1979 | France | |

*Primary Examiner*—Alfred E. Smith
*Assistant Examiner*—T. N. Grigsby
*Attorney, Agent, or Firm*—Watts, Hoffman, Fisher & Heinke Co.

[57] ABSTRACT

An x-ray tube voltage generator with automatic stabilization circuitry is disclosed. The generator includes a source of pulsating direct current voltage such as from a rectified 3 phase transformer. This pulsating voltage is supplied to the cathode and anode of an x-ray tube and forms an accelerating potential for electrons within that tube. The accelerating potential is stabilized with a feedback signal which is provided by a feedback network. The network includes an error signal generator which compares an instantaneous accelerating potential with a preferred reference accelerating potential and generates an error function. This error function is transmitted to a control tube grid which in turn causes the voltage difference between x-ray tube cathode and anode to stabilize and thereby reduce the error function. In this way stabilized accelerating potentials are realized and uniform x-ray energy distributions produced.

18 Claims, 5 Drawing Figures

CONSTANT POTENTIAL H-V GENERATOR

This is a continuation of application Ser. No. 081,779 filed Oct. 4, 1979 and now abandoned.

BACKGROUND OF THE INVENTION

1. Field of The Invention

This invention relates to an improved high voltage generator for providing energy to a computed tomography (CT) scanning x-ray tube. More particularly, the apparatus includes a high voltage stabilization circuit for reducing fluctuations in x-ray energy production.

2. Prior Art

In order to generate x-radiation for CT scanning, an x-ray tube including an anode and cathode electrode is positioned in close proximity to a patient and x-radiation from that tube is transmitted through the patient to an array of x-ray intensity detectors. The intensity data is used in a reconstruction algorithm to provide a density mapping of a patient cross-sectional area. To generate the x-rays, electrons from the cathode are accelerated to the anode due to the force exerted on them by an electric field between the two electrodes. This field is proportional to an electric potential difference applied between those electrodes.

Fluctuations in the voltage separation between cathode and anode result in fluctuations of the electric field and therefore fluctuations in the speed with which the electrons strike the anode material. As the electrons strike the anode, their kinetic energy is transferred to x-radiation energy and heat energy which is dissipated by the anode. Variations in electron kinetic energy result in variations of x-ray energy emitted by the x-ray tube. It is apparent, therefore, that variations or fluctuations in the electrical potential difference between the cathode and the anode result in fluctuations or variations in the energy of x-radiation emitted by the x-ray tube.

The reconstruction of a cross-sectional density mapping by a CT scanner requires accurate intensity information regarding the x-radiation which was passed through the patient. To reconstruct these images it is advantageous to have non-varying accelerating potentials across the x-ray tube to achieve stable x-ray generation and therefore accurate reconstruction images. To generate x-rays the accelerating potential is provided by a high voltage generator which must provide stable voltages of the order of one hundred thousand volts.

One prior art constant potential generation technique is disclosed in the U.S. Pat. No. 3,325,645 entitled "X-Ray Tube System With Voltage and Current Control Means" which has been assigned to the assignee of the present invention. The apparatus embodied in that prior art disclosure includes an alternating high voltage source whose output is, first coarsely adjusted, rectified and then smoothed or filtered with a capacitor. This filtered signal is then transmitted to an x-ray tube cathode and provides the accelerating potential for electrons in the x-ray tube.

Fine adjustment in the accelerating potential is achieved by a feedback control circuit which modulates the amplitude of the signal reaching the filtering capacitor. By modifying the unfiltered high tension voltage in response to the voltage appearing at the x-ray tube the accelerating potential is stabilized. An increase in the filtered signal results in a change in the impedance of the feedback control circuit which tends to reduce the unfiltered signal. Conversely a decrease in the filtered signal results in a change in the impedance of the feedback circuit which tends to add or increase that unfiltered signal. This negative feedback control reduced variations in accelerating potential by reducing the ripple in the filtered high voltage signal.

While achieving substantial commercial success especially in the application for which it was designed, x-ray diffraction, the prior art apparatus disclosed in U.S. Pat. No. 3,325,645 contains some disadvantageous features when applied to CT. One such feature is the utilization of the filtering capacitor to smooth a pulsating signal. Such a capacitor charges to a voltage of many thousands of volts and can retain a substantial amount of stored energy. In CT applications this stored energy can present a safety hazard to both service personnel and to the x-ray tube.

The prior art voltage generator has a limited range of feedback control. If the unfiltered voltage from a transformer secondary in the prior art circuit deviated from a certain range the feedback control circuit could no longer stabilize the accelerating potential. For stabilization beyond this limited effective range a primary transformer control circuit is required to return to the proper range the output from the secondary transformer to the filter capacitor. This limitation added complexity to the stabilization circuit. Finally, the commercial embodiment of the '645 patent operated at too low an accelerating potential and current range for optimum CT use.

SUMMARY OF THE INVENTION

A system utilizing the present invention overcomes disadvantages in prior art high voltage generators by utilization of a differential feedback circuit which maintains the electrical potential difference between anode and cathode of an x-ray tube at a stabilized value. The invention provides a range of dynamic control over this electron accelerating potential large enough to obviate the need for filtering capacitors. No primary transformer control is needed during a CT exposure. A primary transformer control is applied prior to the exposure. Stabilized high voltage is then maintained by the dynamic control which is flexible enough to take into account normal power line fluctuations.

As is conventional the invention uses a source of alternating current in the form of a three phase transformer which generates an alternating current signal. This signal is rectified and transferred to an electrode on the x-ray tube and provides an accelerating voltage to cause electron flow to the tube anode. If this rectified pulsating signal were used directly to accelerate electrons from the cathode, these electrons would accelerate according to the pulsating potential from the three phase transformer and generate non-uniform x-rays when striking the anode.

A system of the present invention, however, causes the accelerating potentials to be modified in such a way that uniformity in accelerating potential is achieved. A signal proportional to the actual accelerating potential on the x-ray tube is compared with a reference signal which is proportional to a desired or optimum accelerating potential. As the reference signal is compared to the actual accelerating potential, an error signal is generated and used as a feedback signal which controls modification of the x-ray tube accelerating potential. A control tube in a feedback control circuit provides the means for stabilizing the accelerating potential.

The tube includes a control grid which forms a portion of the feedback circuit. When the grid potential is modified in response to the error signal, electron flow in the control tube is modified and as a result the accelerating potential appearing at the x-ray tube electrode is changed. This negative feedback allows an unfiltered signal to be used to accelerate electrons in the x-ray tube. The dynamic range of the control tube is large enough to effectively modulate the output of the rectified alternating current. No capacitors are needed and thus no charge build up occurs which might present a danger to service personnel or to the x-ray tube.

In one embodiment of the invention the source of alternating voltage comprises two three phase transformer secondaries with full wave rectification for providing two pulsating DC voltages. One of these voltages is above ground and the other below ground and it is the difference in these voltages which appears across the cathode and anode of the x-ray tube. Both secondary transformers are energized by the same primary but their outputs are not symmetric about ground potential. Instead, one pulsating DC signal leads the other so that the voltage difference between the two signals has a periodicity of 12 cycles per one primary energization cycle. As noted above this periodicity would adversely affect x-ray generation but for operation of the differential feedback control featured in the preferred embodiment of the invention.

As the two pulsating DC voltages are sent to the anode and cathode of the x-ray tube the difference between them is sensed and a signal proportional to this difference is generated. It is this signal which is compared to a reference signal for generation of an error signal. Once this error signal has been generated, it is transmitted to two control tubes connected to the x-ray electrodes. One tube forms a variable impedance path between the x-ray tube cathode and ground and the other control tube provides a second variable impedance path between the x-ray anode and ground. Modification of the voltages on the control grids of these tubes modifies the control tube impedance, thereby varying the voltage appearing at the x-ray tube anode and cathode. The impedance on these two tubes is changed in such a way that the difference in voltage across the x-ray tube is stabilized.

In the preferred embodiment of the invention one control tube is connected in a standard cathode grounded configuration and the other control tube has its anode grounded with its control grid and cathode at a voltage on the order of 10,000 volts negative. Since fluctuations in the control grid voltage are used to vary the control tube impedance, the invention must provide a way to accurately transmit the error signal to this high voltage level and modify the grid potential. To accomplish this function an electrical isolation coupling is provided.

The isolation coupling sends the error signal to the high voltage grid by a frequency modulated transmission system utilizing an optical coupler. The error signal is transmitted to a frequency modulation driver which sends the information contained in the signal to a high voltage frequency modulation receiver which is tied to a high common potential, which in one embodiment is the cathode potential of the grounded anode tube. The error information is again converted to a voltage and used to modulate the grounded anode control tube grid. In this way a relatively low voltage error signal can be used to modulate a control grid at a very high potential without disrupting the low voltage portions of the feedback circuitry.

In the two control tube embodiment of the invention, a wide range of control is made possible through a second feedback circuit which continuously maintains the control tubes in an active region of operation and prevents either tube from either saturating or going into a cutoff state of operation. To achieve this function, the non-grounded electrodes of the two control tubes are monitored to determine what voltages appear at these non-grounded electrodes. A control signal proportional to these voltages is generated and sent to a summing amplifier in a separate portion of the feedback circuit. The output from this summing amplifier is added to the error signal before the combined signal is transmitted to the control grid of one control tube. Should the biasing of one or the other of the control tubes deviate from an optimum operating range, this second feedback portion of the circuit will tend to modify the voltage appearing at the control tube non-grounded electrode and return the tube to its proper operating range. Once the voltage on this non-grounded electrode control tube is modified the system automatically adjusts the voltage on the second control tube.

From the above it is apparent that one object of the present invention is to provide a stabilized high voltage accelerating potential difference between the anode and cathode of an x-ray tube. One advantageous feature of the differential feedback control embodied in the invention is the wide dynamic range of the system which allows for stabilization without the utilization of filtering capacitors. This lack of potentially dangerous filtering capacitors is one obvious advantage the system has over the prior art.

A second objective of the present invention is to provide a differential control circuit wherein a control tube's operating characteristics are monitored and controlled to provide x-ray generating potential without the need for a circuit to continuously control the voltage input to the system and appearing across the transformer primary.

A further feature of the invention is the utilization of electrical isolation circuitry which allows a low voltage error signal to be transmitted to a high electrical potential control grid by the use of an optically coupled circuit. The electrical isolation is achieved through a frequency modulated transmitter and receiver arrangement which advantageously utilizes an optically coupled rather than an electrically coupled portion of the feedback loop.

Other features and advantages of the invention will become better understood when the description of a preferred embodiment of the invention is considered in conjunction with the accompanying drawings.

PREFERRED EMBODIMENT OF THE INVENTION

Figure 1:
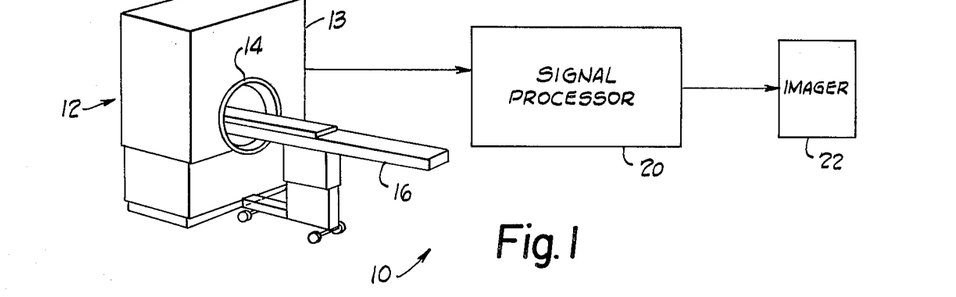
FIG. 1 is a schematic of a CT scanning unit.

FIG. 1 shows a computed tomography system 10 used for examining the internal structure of a patient. The unit comprises a scanning unit 12, couch 16, signal processor 20 and imager 22. The scanning unit 12 is mounted to a floor and remains stationary relative to the patient. The scanning unit includes a housing 13 which covers x-ray apparatus including an x-ray tube which rotates for CT scanning. The housing 13 is constructed to include an aperture 14. The couch 16 is movably mounted and is operative to position the patient within the aperture 14 for x-ray scanning. The signal processor 20 and the imager 22 are electrically connected to the scanning unit. The scanning unit obtains x-ray intensity data and sends this intensity data to the signal processor. The x-ray intensity data is then processed by the signal processor to obtain information concerning the relative densities of a patient cross-section of interest. This density data is transferred to the imager where the doctor can view the relative density information on a viewing screen.

Figure 2:
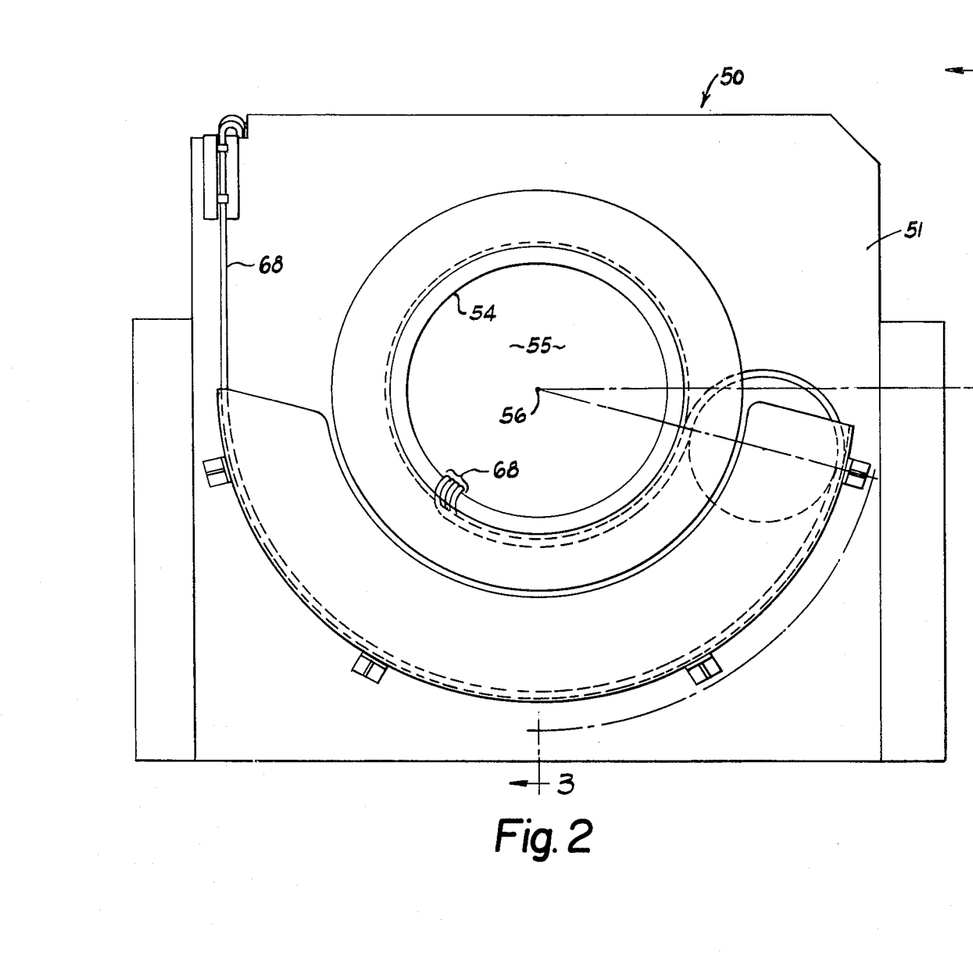
FIG. 2 is a rear elevational view of a CT machine with its housing removed.
Figure 3:
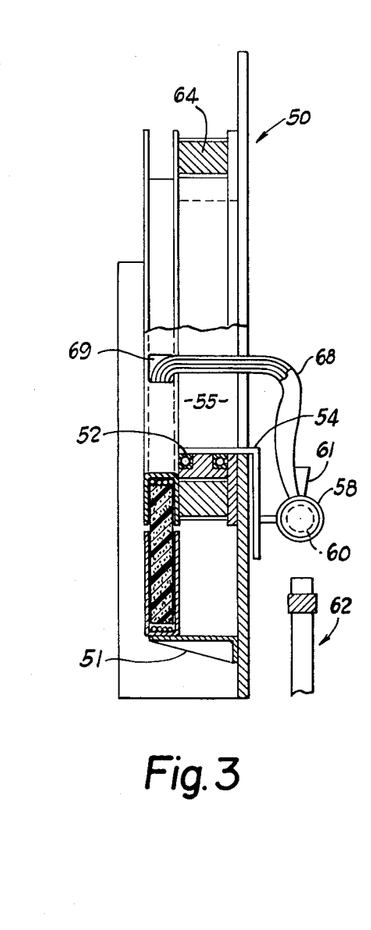
FIG. 3 is a sectional view of the CT scanner of FIG. 3 as seen from the plane indicated by the line 3—3 of FIG. 2.

Referring to FIGS. 2 and 3, an x-ray tube support and manipulating assembly comprising a stationary detector scanning unit is shown generally at 50. The assembly 50 includes a housing and frame structure 51. A pair of spindle bearings 52 are carried by the housing and frame structure 51, (see FIG. 2). A tubular spindle 54 is journaled in the bearings 52. The spindle 54 delineates a patient receiving opening 55. When the scanner is in use, a patient is supported on a stretcher with portions of the patients body disposed within the opening 55.

An x-ray tube assembly 58 (see FIG. 3) is fixed to the tubular spindle for orbital rotation about an axis 56 of the spindle 54 and the opening 55. The x-ray tube assembly includes an x-ray tube indicated by the dotted line 60, a collimator shown diagrammatically at 61, and other known and conventional components of an x-ray tube assembly of the type used in CT studies.

The tube support and manipulating assembly 50 shown in FIGS. 2 and 3 is of a machine of the stationary detector type. For clarity of illustration, and because the detector array is now known in the art, the annular detector array which is around the orbital path of the x-ray tube assembly 58 is not shown except in a fragmentary schematic way at 62 in FIG. 3.

In use, the x-ray tube is orbited about the axis 56 over a range of orbital motion over a path of sufficient length to accelerate the tube to its full speed for a study, a 360° scan and deceleration through an additional orbital path which is long enough to permit the tube to be smoothly brought to a stop. The orbital motion is first in one direction and then the other. Expressed another way, the tube may be moved a range in a clockwise direction and then counterclockwise on the next study.

A drive for this orbital motion is shown schematically and it includes an annular motor 64 which is connected to the spindle 54. The drive shown is for schematic illustration only. Any of the known and commercially accepted drive systems can be employed.

Four flexible conduits or cables 68 are connected to the x-ray tube assembly 58. These cables include conductors for supplying electron accelerating potential for the x-ray tube, for collimator and filter adjustment, and such other power requirements the tube assembly may have. The cables 68 extend from the x-ray tube through the opening 65 where they are adjacent the spindle 54 and into a cable delivery opening 69 (see FIG. 3).

The accelerating potential is supplied by a voltage generator embodying a stabilization circuit. The stabilization circuit maintains the potential at a highly constant level thereby insuring the x-radiation is of a constant mean energy level.

Figure 4:
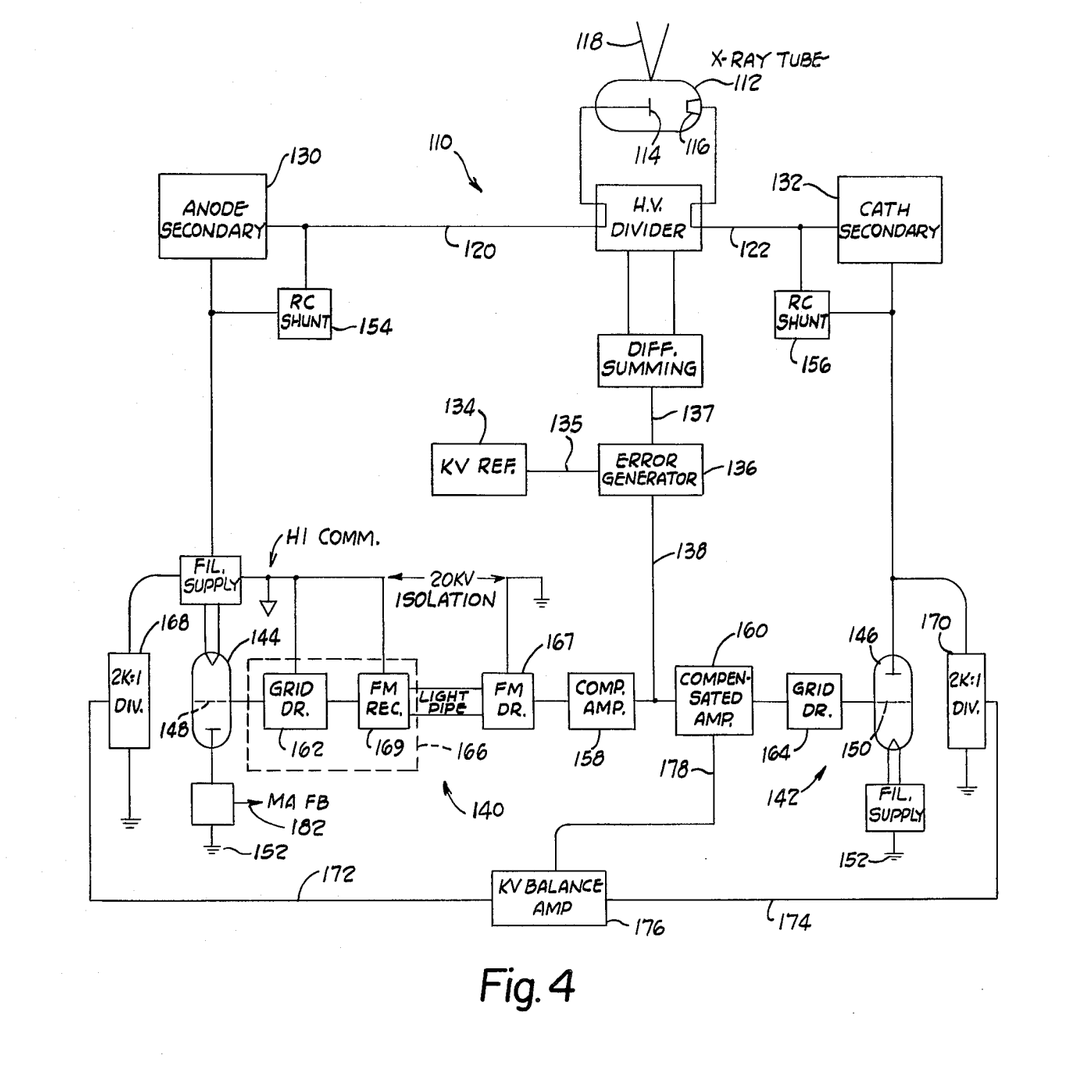
FIG. 4 is a schematic representation of the improved x-ray potential generator embodying the invention.

Referring now to FIG. 4, a high voltage generator for an x-ray tube 112 is shown schematically at 110. The x-ray tube 112 has an anode 114 and cathode 116 electrically connected to the generator 110. An input 120 transmits a potential to the anode 114, and a second input 122 to the cathode 116. The potential difference between these two inputs causes electrons emitted by the cathode to accelerate toward the anode. When the accelerated electrons strike the anode their kinetic energy of motion is transformed into heat and x-radiation energy 118.

To provide a voltage differential to the anode and cathode, the generator 110 includes a source of alternating voltage which in the embodiment shown comprises two high voltage transformers secondary circuits 130, 132. One transformer secondary 130 produces a signal which is rectified and sent to the x-ray tube anode, the second transformer secondary 132 produces a second signal which is also rectified and sent to the x-ray tube cathode. Although the outputs from these secondaries are rectified, they are not filtered and therefore comprise pulsating DC signals. In the preferred embodiment the output from a first secondary 130 is rectified to provide a voltage above ground potential and the other output is rectified to produce an output below ground potential. Although the secondary transformers are driven by the same primary, the existence of other components within the circuitry produces a phase shift between the two pulsating signals and therefore the signals are not symmetric above and below ground. Due to this factor, an irregular shaped, pulsating potential difference is supplied between the cathode and anode of the x-ray tube. It is the function of the remainder of the circuitry within the generator 110 to smooth and stabilize this potential difference in order that the electrons accelerated in the x-ray tube have a stable average kinetic energy and therefore the x-radiation produced has a stabilized mean value.

To achieve this stabilized energy, the generator 110 further comprises a reference generator 134, an error generator 136, and responsive to the output 138 from the error generator. The reference generator produces a voltage output or signal 135 which is proportional to a desired potential difference between cathode and anode of the x-ray tube. This reference signal 135 is a constant value voltage and is proportional to the proper accelerating potential to produce a desired average or mean fan beam x-ray radiation energy. This signal is sent to an error generator 136 which compares the signal 135 with an input 137 which is proportional to the potential difference appearing across the anode and cathode of the x-ray tube. But for the advantageous operation of the feedback loop system of the generator 110 this input signal 137 would comprise a pulsating potential proportional to the voltage difference supplied by the transformer secondaries. Due to the advantageous operation, however, of the feedback technique embodied by the invention, the pulsating output from these secondaries is modified and the accelerating potential across the tube anode and cathode is stabilized at the reference value.

The output from the error generator 136 is a voltage signal which is proportional to the difference between the optimum or reference input 135 and the actual potential difference appearing across the x-ray tube. This output 138 is an error signal and is used as an input to a in such a way that the potential difference between anode and cathode of the x-ray tube is stabilized even though the output from the transformer secondaries remains a pulsating d.c. signal.

In an embodiment where two transformers' secondaries provide the accelerating potential difference to the x-ray tube, two feedback portions 140, 142 are required in the generator 110. Each portion includes a control tube 144, 146 with a control grid 148, 150. The error signal 138 is sent through each of the feedback portions and modifies the control tube grid voltage in such a way that the signal sent to the x-ray tube electrodes 114, 116 from the transformer secondaries is modified and the potential difference appearing across the tube is stabilized at the constant reference value.

As seen in FIG. 4, each control tube 144, 146 comprises a portion of an electrical path between the secondary transformers 130, 132 and electrical ground 152. By modifying the voltage on the grids 148, 150 of the control tubes the impedance these control tubes presents is altered in such a way that the error signal 138 will be minimized. To insure that a change in control tubes impedance is transmitted as a signal to the x-ray tube electrodes, two shunt paths 154, 156 by-pass the transformer secondaries and transmit signals resulting from the change in control tube impedance to the x-ray tube cathode/anode 114, 116. These shunt paths represent a low impedance path for alternating current signals generated through control of the control grids 148, 150 and allow these AC signals to moderate fluctuations in accelerating potential. The voltage appearing at either electrode therefore comprises two portions; the output from a transformer secondary and the control signal passing through the shunt path from the control tube.

As an illustration, assume that the voltage difference between the cathode and anode of the x-ray tube is smaller than an optimum value. That is, the desired accelerating potential is greater than the instantaneous actual accelerating potential appearing across that tube. When this condition exists the x-ray beams emitted by the tube have an average energy less than an optimum desired value. Under these circumstances comparison of the two signals 135, 137 entering the error generator 136 will cause an error output signal 138 to be sent to the grids 148, 150. In actual operation, it is not the error signal 138 but an amplified signal which is used to control the voltage on the two grids. This amplification is achieved by sending the signal through two compensating amplifiers 158, 160 and then through two grid drivers 162, 164. The voltage output on the grid drivers will modify the voltage on the grids 148, 150 to increase the x-ray tube anode/cathode voltage differential and thereby bring this value in conformity with an optimized or reference voltage. If as was postulated the anode to cathode voltage differential is to be increased, the potential drop across the control tubes 144, 146 must be decreased through modification or adjustment of the grid potentials.

It should be appreciated that the grid potential does not stabilize at an optimum value and that instead the system operates in a dynamic feedback mode. The rectified outputs from the transformer secondaries are pulsating voltages so that the grid drivers 162, 164 must continually adjust as the error signal generated in the error generator changes. The feedback circuitry responds quickly enough to the pulsating DC voltage to achieve voltage stabilization. This stabilization requires no filtering compacitors and is satisfactory for accurate computed tomography x-ray generation.

The two control tubes 144, 146 included in the feedback portions 140, 142 perform similar functions yet due to the opposite polarity of the cathode and anode x-ray tube potentials, the two tubes are configured differently. One control tube 144 has its anode essentially grounded and the second 146 tube has its cathode very close to ground. The opposed (non-grounded) electrodes are many thousand volts removed from ground with the grounded anode tube having its filament well below ground and the grounded filament tube having its anode well above ground.

To control the flow of electrons in the control tubes, the control grid voltage must be held in a range near the filament voltage. For the grounded filament tube 146 this constraint presents no problem. Its grid 150 potential is maintained slightly below ground and may be increased to a value of approximately 150 volts negative. Modification of this voltage by the grid driver 164 modifies the flow of electrons in that tube 146 and therefore modifies the impedance between ground and the cathode of the x-ray tube.

The constraint on the other grid 148 presents control problems since that grid must be maintained at a potential on the order of the non-ground filament potential which is approximately 10,000 volts below ground. The problem presented is to send a control function proportional to the error signal to a control grid 148 which is maintained at a potential of approximately 10,000 volts. Electrical coupling between the high voltage grid and the low voltage error signal would result in voltage spikes, arcing, and current flows of unsuitable magnitude. Avoidance of these problems has been achieved by the inclusion of an electrical isolation circuit portion 166 interposed between the error signal compensation amplifier 158 and the high potential grid driver 162.

The isolation portion 166 comprises a frequency modulated receiver 169 interconnected through a light pipe to a frequency modulated driver 167. The error signal is sent to the frequency modulation driver 167 which transforms the voltage signal into a frequency modulated signal. The frequency modulated signal is transmitted through the light pipe to the frequency modulated receiver which decodes the frequency modulated information and returns it into the form of an electrical voltage signal. The light pipe is, of course, an electrical insulator and therefore the high potential on the grid 148 does not affect the low potential portions of the generator 110. The coding and decoding of information through the electrical isolation portion 166 is achieved by amplitude modulating with a 160 kilocycle frequency modulated subcarrier, a light beam signal. Techniques for modifying this signal in such a way as to carry the error signal information are known. One optical coupling system capable of performing such functions is commercially available from Burr-Brown. That system comprises a model 3712T transmitter, a model 3712R receiver and fiber optic coupling.

Connected to the non-grounded electrodes of each control tube are two voltage dividers 168, 170. These dividers function in helping maintain the two control tubes 144, 146 within a dynamic range of operation.

Two outputs 172, 174 from the dividers 168, 170 are transmitted to a summing or balancing amplifier 176. This amplifier 176 receives these two signals and produces an output proportional to their algebraic sum. As appreciated by those skilled in the art, the output 172 from one voltage divider 168 is a signal proportional to the output on the non-grounded filament of the grounded anode control tube 144. The output 174 from the other divider is proportional to the voltage appearing at the anode of the grounded filament control tube 146. To maintain the differential in voltage across the cathode and anode of the x-ray tube these values need not be equal, but to insure control tube operation is maintained in a dynamic range of operation (i.e. neither tube goes into saturation or cutoff) an output 178 from the summing amplifier 176 is used to modify the error signal 138 emitted by the error generator. This modification maintains each non-grounded control tube electrode at approximately the same absolute voltage from ground and thereby maintains the control tube in an effective operating range to dynamically control x-ray tube potential differences. But for the utilization of this balancing or summing amplifier 176 it is possible that while the potential difference across the x-ray tube cathode and anode 114, 116 would be maintained at a relatively stable value, one control tube voltage drop would be substantially less than the other and at some time the feedback stabilization circuitry would fail due to either cutoff or saturation of one or the other of the control tubes. Operation of the summing or balancing amplifier in the feedback loop maintains the voltage drop across each control tube at approximately equal absolute values. Modification of the voltage on the tube control grids 248, 150 continues to maintain the difference in potential across the x-ray tube at a constant level.

Figure 5:
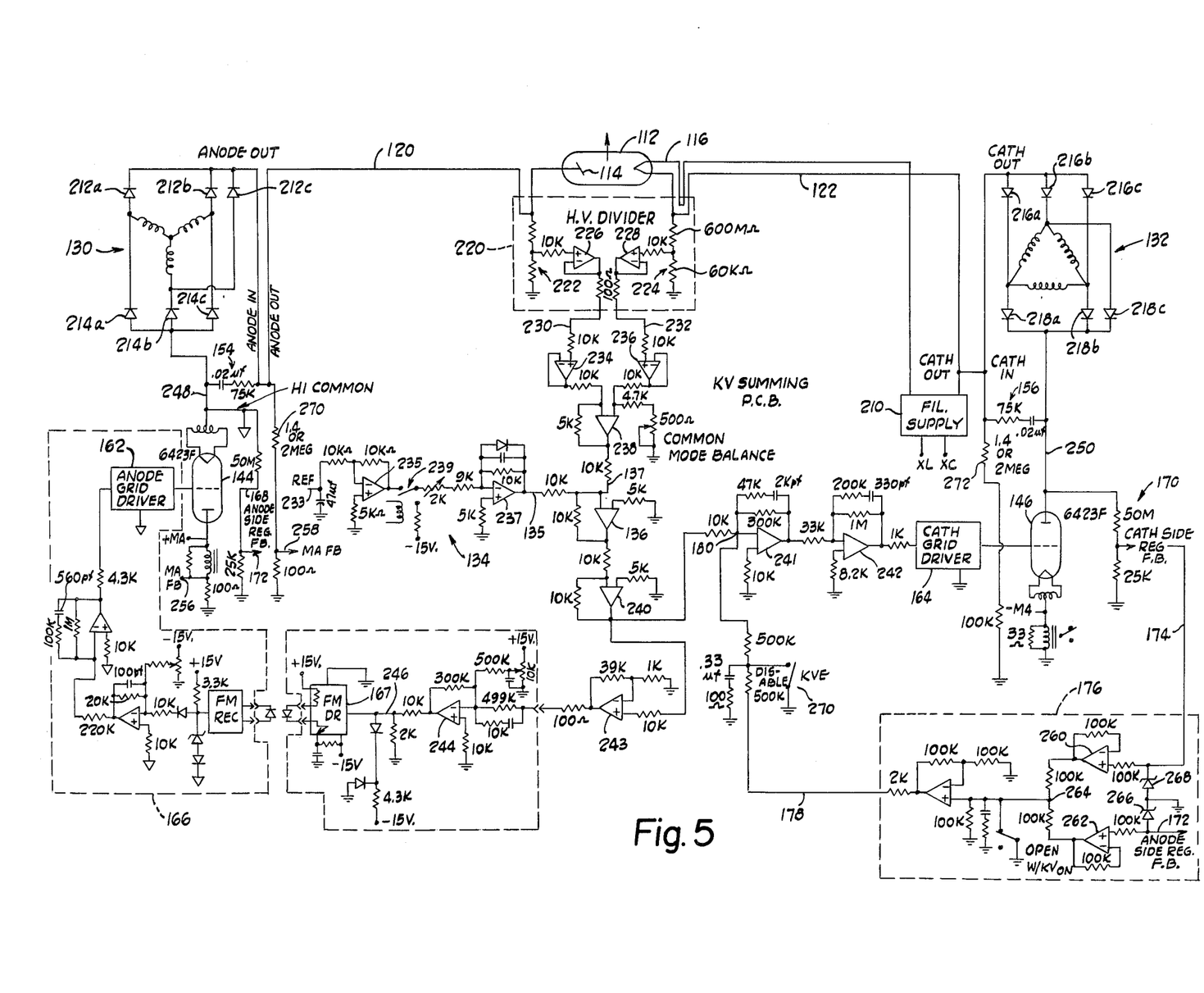
FIG. 5 is a more detailed schematic of the representation illustrated in FIG. 4.

Turning now to FIG. 5, a detailed schematic of the system shown broadly in FIG. 4 is presented. As noted above a voltage from two inputs 120, 122 appears across the anode 114 and cathode 116 of an x-ray tube 112. Electrons are emitted from the cathode 116 in response to a current flow generated by a filament supply 210. They accelerate across the x-ray tube, strike the anode 114, and x-radiation is emitted.

The high voltage is necessary to accelerate electrons to a sufficiently large kinetic energy to create x-radiation. This voltage is provided by two secondary transformers 130, 132. One secondary 130 is configured in a wye format and the second secondary 132 is configured in a delta format. Outputs from the delta and the wye secondary windings are rectified by a number of diodes attached to these outputs. Diodes 212a–c and 214a–c serve to rectify the output from the wye transformer secondary and a second set of diodes 216a–c and 218a–c serve to rectify the output from the delta transformer. Were it not for the feedback operation of the present generator, the outputs from these rectified transformer secondaries would be pulsating DC potentials and would provide an irregular pulsating accelerating potential to the x-ray tube.

The feedback correction circuit includes a high voltage divider 220 which produces lower voltage signals representing the high voltages appearing at the cathode and anode of the x-ray tube. These smaller magnitude voltages are more suitable to serve as control functions in the feedback portions of the x-ray stabilization generator. The high voltage divider 220 comprises a first 222 and second 224 voltage divider which reduces the high input from the anode and cathode by a factor of 10,000. The output from these two voltage dividers is transmitted to two power amplifiers 226, 228.

Two outputs 230, 232 leave the high voltage divider 220 and are transferred through a second pair of power amplifiers 234, 236. These two outputs form inputs to a differential amplifier 238. The output from the differential error amplifier 137 is a signal proportional to the absolute voltage difference between the high voltage appearing between the cathode and anode. In a preferred embodiment shown in FIG. 5 a voltage separation of 20 kv produces an output 137 from the differential amplifier 238 of one volt.

As noted previously, a reference generator 134 provides an output 135 proportional to a preferred or desired accelerating potential. In the preferred embodiment of the invention a one volt signal appears at the output 135 for each 20,000 volts of desired accelerating potential. The output 135 is generated by a reference input 233 and two amplifiers 235, 237. The input 233 is transmitted to the output 135 only during a patient exposure. A switch 239 completes the circuit during exposures and at other times completes a connection to a −15 volt power supply.

The two outputs 135, 137 from the reference generator 134 and the differential amplifier 238 respectively are summed by a summing or error generator 136. If the instantaneous voltage appearing across the cathode and anode of the x-ray tube is equal to the desired accelerating potential the output from the error generator will be zero volts. A difference between the actual instantaneous accelerating potential and the desired or reference signal produces either a positive or negative voltage output from the error generator 136 which is used to modify the grid potentials on the two control tubes.

A plurality of operational amplifiers 240–242 are included which transmit the error signal to a cathode grid driver 164 which modifies voltages appearing upon the grounded filament tube control grid. Other amplifiers 243, 244 transmit the error signal to a frequency modulated driver 167 which in turn transmits the error signal to the isolated portion of the circuit 166. These operational amplifiers 240–244 are inserted to maintain the proper power transfer and also to maintain circuit stability. Without these amplifiers it is possible that under varying feedback conditions the circuitry might go into oscillation and disrupt functioning of the system.

An output 246 from the amplifier 244 forms an input to the frequency modulated driver 167. This driver converts the error signal which has been in the form of a voltage into a frequency modulated signal which can be conveniently transferred to an isolated portion 166 by optically coupled circuitry such as a light pipe. The frequency modulated signal is received by a receiver 169 which reconverts the frequency modulated signal into a voltage signal and transmits it through two amplifiers to the anode grid driver 162. Both anode and cathode grid drivers comprise amplifiers with gains of approximately 150 and a dynamic range of approximately 170 volts. By modulating the voltage output from the two grid drivers it is possible to change the control tube impedances and therefore the voltage drop across these two control tubes. This modification in control tube impedance results in a voltage signal appearing at two outputs 248, 250 on the nongrounded electrodes of the two control tubes. Due to the presence of a shunt path 154, 156 between these points and the x-ray tube anode and cathode respectively this modulated signal appearing on the nongrounded electrodes of the two control tubes is transmitted to the cathode and anode of the x-ray tube. In this way modifications in the control voltage on the control tube grids directly modifies the voltage separation appearing between the cathode and the anode of the x-ray tube and by proper modulation of this control voltage the voltage separation appearing across these two electrodes is maintained at a steady or constant value.

Since it is desirable not only to maintain constant anode-to-cathode voltage of the x-ray tube but also to maintain each control tube in a dynamic range of operation, the nongrounded electrode voltages are also adjusted to insure that they are always at approximately the same voltage value from zero potential. It is important to fix the control tubes in a dynamic range of operation so that the maximum possible control over x-ray tube accelerating potentials is achieved. The voltage appearing at the nongrounded electrodes of the two tubes is monitored and a nonequality in their absolute value (note: one is approximately 10,000 volts above ground and one 10,000 volts below ground) results in a control signal modifying the error signal transmitted to the cathode and anode grid drivers.

Two voltage dividers 168, 170 sample the voltage at the nongrounded electrodes of the two control grids and send a signal proportional to these voltages to a summing amplifier 176. If the two voltages are equal then the output 178 from the summing amplifier is zero volts and the error signal appearing at a junction 180 within the feedback circuit is unmodified. If, however, the two voltages appearing at the nongrounded electrodes are unequal a signal 178 modifies the error signal sent to the cathode grid driver in such a way that the cathode grid driver 164 will modify the grid potential in response to both the error signal and the balance signal. The change is so as to again produce equality between the nongrounded electrodes of the control tubes and maintain them in a dynamic range of operation. Thus, a type of double feedback circuit is arranged to maintain the voltage or accelerating potential across the cathode and anode of the x-ray tube at a constant value, and to maintain the control tubes in a dynamic range of operation to achieve maximum control over the accelerating potential.

The balance portion of the circuit includes two amplifiers 260, 262. These are buffer amplifiers and transmit the signal from the voltage dividers 168, 170 and transmit those signals to a summing junction 264. Also connected to the output of the voltage dividers 168, 170 are two zener diodes 266, 268. These protect the amplifiers 260, 262 from large voltage spikes should either divider 168, 170 have an open circuit in its 25 kΩ resistors.

The balance portion also includes a switch 270 which disables the balance signal 178. When disabled, the constant potential between x-ray tube cathode and anode is maintained but the control tubes' nongrounded electrodes are no longer maintained at the same potential from zero potential. This switch is used for testing and aligning purposes.

Each control tube circuit further includes a larger resistor 270, 272 connected between an x-ray tube electrode and ground. This resistor helps bias the control tubes even at low x-ray tube currents. With the resistors 270, 272 in the circuit, the current passing through the control tubes is equal to the current passing through these large biasing resistors plus the current flowing through the x-ray tube. Other circuits within the system 10 monitor x-ray tube current and modify that current as changes are made in the desired current selection. To accurately monitor the x-ray tube current, two outputs 256, 258 are transmitted to other circuitry not shown in the diagrams. These outputs are combined into one signal proportional to tube current and used to control the output of the filament supply 210.

In the detailed schematic (FIG. 5) preferred values for capacitors and resistors have been given but the high voltage stabilization could be achieved using other component values. A model #6423F control tube is utilized in the preferred circuit.

Although a preferred embodiment has been described, it should be appreciated that design modifications could be incorporated without departing from the spirit or scope of the invention as set forth in the appended claims.

What is claimed is:

1. A high voltage generator couplable to a source of alternating voltage comprising rectification means connected to said source for providing a pulsating DC accelerating voltage; a reference circuit for comparing the pulsating accelerator voltage magnitude with a reference signal and producing an error signal; a dynamic control circuit including a saturable control element responsive to the error signal for modifying the pulsating accelerator voltage for transmission to an x-ray tube electrode, and balancing circuitry comprising means for sensing the voltage across said saturable control element and for maintaining the control element in a non-saturated operating range.

2. The generator of claim 1, further comprising the alternating voltage source including two secondary three phase transformer windings and the rectification means includes diodes connected to windings to provide two pulsating voltages; one above ground and one below ground and means for applying the difference in voltage between the two pulsating voltages to the x-ray tube.

3. The generator of claim 2 which further comprises two voltage dividers for generating reduced pulsating voltages and a difference amplifier for generating a signal equal to the difference between these reduced pulsating voltages.

4. The generator of claim 3 wherein the control circuit comprises two feedback circuits with two control tubes coupled to the x-ray tube; said feedback circuits connected for transmitting the error signal to each tube thereby modifying the accelerating potential.

5. The generator of claim 4 wherein one feedback circuit comprises an optically coupled isolation means for transmitting the error signal to a control tube grid electrically isolated from the reference circuit.

6. The generator of claim 4 wherein one control tube has a grounded anode and a second control tube has a grounded cathode, the control tube non-grounded electrodes coupled to the x-ray tube electrodes.

7. A method for stabilizing an electron accelerating potential in an x-ray tube, said method comprising the steps of:
(a) generating two pulsating direct current voltages of opposite polarity;
(b) sensing the instantaneous difference between said two voltages;
(c) producing an error signal by comparing the sensed difference with a reference voltage;
(d) modifying by use of two control tubes the two pulsating voltages for minimizing the error signal independently of smoothing of the pulsating voltages, and (e) adjusting the error signal in response to anode to cathode x-ray tube potential for maintaining x-ray tube potential at the reference value.

8. A method for stabilizing an electron accelerating potential in an x-ray tube, said method comprising the steps of:

(a) generating two pulsating direct current voltages of opposite polarity;

(b) sensing the difference between the two voltages;

(c) generating an error signal by comparing the difference with a reference voltage;

(d) modifying by the use of two saturable control tubes the two pulsating voltages to minimize the error signal by adjustment of two control tube grid potentials, said control tubes being inserted between the two pulsating direct current voltages and electrical ground, and (e) adjusting the error signal to maintain the anode to cathode electrical potential difference of the x-ray tube at a stabilized level.

9. The method of claim 8, further comprising the step of transmitting the error signal to one control tube grid through an optically coupled isolation circuit.

10. The method of claim 8, further comprising the step of sensing an electrode potential for each control tube and controlling the grid potentials in response to the electrode potential.

11. The method of claim 10, wherein the sensed electrode is electrically coupled to the x-ray tube and comprises a non-grounded electrode.

12. An x-ray tube voltage generator comprising:

(a) a source of alternating current;

(b) a first transformer circuit energized by said source to produce a first pulsating DC signal;

(c) a second transformer circuit energized by the source to produce a second pulsating DC signal opposite in sign to said first signal, and (d) dynamic control circuitry including two control tubes each having one of its anode and cathode substantially at ground potential, said control tubes being connected to said first and second transformer circuits to stabilize the potential difference across the x-ray tube, said controlled circuitry comprising:

(i) said control tubes each being a triode;

(ii) circuitry for producing signals representing anode to ground and cathode to ground potential of each of the control tubes, and (iii) control circuitry responsive to said control tube potential representing signals for maintaining control tube operation with a substantially non-saturated dynamic range.

13. The generator of claim 12, wherein a portion of the control circuit is electrically isolated by optical coupling apparatus.

14. A high voltage generator couplable to a source of alternating voltage including two secondary three-phase transformer windings; rectification means including diodes connected to the windings to provide two pulsating voltages; one above ground and one below ground with the value of the difference in voltage between the two pulsating voltages equal to the accelerating voltage; a reference circuit for comparing the pulsating accelerating voltage magnitude with a reference signal and producing an error signal; a control circuit responsive to the error signal for modifying the pulsating accelerator voltage for transmission to an x-ray tube electrode, said control circuit comprising two circuits with two control tubes coupled to the x-ray tube, said circuits connected for transmitting the error signal to each control tube thereby modifying the accelerating potential, and wherein one control tube has a grounded anode and a second control tube has a grounded cathode, the control tube non-grounded electrodes coupled to the x-ray tube electrodes; said generator further comprising two voltage dividers for generating reduced pulsating voltages and a difference amplifier for generating a signal equal to the difference between these reduced pulsating voltages.

15. An x-ray tube voltage generator comprising:

(a) a source of alternating current;

(b) a first transformer circuit energized by said source to produce a first pulsating DC signal;

(c) a second transformer circuit energized by the source to produce a second pulsating DC signal opposite in signal to said first signal; and, (d) dynamic control circuitry including two series coupled control tubes each having one of its anode and cathode substantially at ground potential, said control tubes being connected to said first and second transformer circuits to stabilize the potential difference across the x-ray tube.

16. The generator of claim 15 wherein the control circuitry comprises:

(a) said control tubes each being a triode;

(c) circuitry for producing signals representing anode to grid and cathode to grid potential of each of the control tubes, and (c) control circuitry responsive to said control tube potential representing signals for maintaining control tube operation within a substantially non-saturated dynamic range.

17. The generator of claim 16 wherein a portion of the control circuit is electrically isolated by an optical coupling apparatus.

18. An automatic stabilizing x-ray tube voltage generator comprising:

(a) a source of alternating voltage;

(b) a first and second rectification means connected to the source for producing two pulsating DC voltages; one DC voltage having an average potential above ground and a second having an average potential below ground;

(c) means for producing a difference signal representing the potential difference between the two pulsating DC voltages;

(d) a reference generator for providing a signal proportional to an optimum voltage difference; said optimum voltage difference equal to a desired acceleration potential for an x-ray tube;

(e) an error amplifier for comparing said reference signal with the difference signal and producing an error signal;

(f) control circuitry including two saturable control tubes responsive to the error signal for modifying the output from the two rectification means to minimize the difference between the optimum voltage and the instantaneous voltage, and (g) balance circuitry comprising means for sensing the voltage across each control tube for maintaining the control tubes each in a non-saturated operating range.

* * * * *

UNITED STATES PATENT AND TRADEMARK OFFICE
CERTIFICATE OF CORRECTION

PATENT NO. : 4,453,263
DATED : June 5, 1984
INVENTOR(S) : THEODORE A. RESNICK et al It is certified that error appears in the above-identified patent and that said Letters Patent is hereby corrected as shown below:

Column 11, line 61, "larger" should be --large--;

Column 13, line 53, "with" should be --within--;

Column 14, line 31, "(c)" should be --(b)--;

Signed and Sealed this

Second Day of October 1984

[SEAL]

Attest:

GERALD J. MOSSINGHOFF

Attesting Officer

Commissioner of Patents and Trademarks